United States Patent [19]
Fretz, Jr.

[11] 4,377,653
[45] Mar. 22, 1983

[54] MIXED ETHER COMPOSITIONS CONTAINING OLIGOMERS OF POLYFUNCTIONAL PHOSPHINE OXIDES: FLAME RETARDANTS FOR POLYMERS

[75] Inventor: Edward R. Fretz, Jr., East Windsor, N.J.

[73] Assignee: FMC Corporation, Philadelphia, Pa.

[21] Appl. No.: 229,706

[22] Filed: Jan. 30, 1981

[51] Int. Cl.³ .......................... C08K 5/53; C07F 9/53
[52] U.S. Cl. ...................................... 524/129; 568/15; 523/506
[58] Field of Search ................. 260/45.95 G, 45.95 P, 260/45.95 S; 568/14, 15; 521/108; 528/72, 167, 169, 287; 524/129

[56]  References Cited
U.S. PATENT DOCUMENTS

| | | | |
|---|---|---|---|
| 2,882,321 | 4/1959 | Dornfeld | 260/606.5 |
| 3,248,429 | 4/1966 | Baranauckas et al. | 568/13 |
| 3,258,492 | 6/1966 | Ritt | 568/14 |
| 3,267,149 | 8/1966 | Garner | 260/45.95 P |
| 3,332,962 | 7/1967 | Grayson et al. | 260/332.3 |
| 3,333,005 | 7/1967 | Grayson et al. | 260/606.5 |
| 3,404,187 | 10/1968 | Kober et al. | 260/606.5 |
| 3,474,981 | 3/1969 | Baranauckas et al. | 260/2.5 |
| 3,477,953 | 11/1969 | Carlson | 568/15 |
| 3,716,580 | 2/1973 | Maier | 568/13 |
| 3,732,316 | 5/1973 | Lin | 260/606.5 P |
| 3,779,953 | 12/1973 | Papa | 568/72 |
| 3,883,474 | 5/1975 | Racky et al. | 260/45.75 |
| 3,883,476 | 5/1975 | Racky et al. | 260/45.75 |
| 4,063,934 | 1/1978 | Moedritzer et al. | 260/931 |

Primary Examiner—Veronica P. Hoke
Attorney, Agent, or Firm—Robert W. Kell; Frank Ianno

[57]  ABSTRACT

Mixed ether compositions containing oligomers of polyhydroxyalkyl phosphine oxide are prepared by heating a polyhydroxyalkyl phosphine oxide in the presence of an acid catalyst at temperatures within the range of from about 139° C. to about 200° C. and removing water from the reaction mixture. When the reaction is conducted in the presence of an aliphatic, cycloaliphatic or aromatic alcohol having one or more hydroxyl groups mixed phosphine oxide ethers of the added alcohol are formed. The mixed ether compositions of the present invention are useful fire retardant additives.

73 Claims, No Drawings

MIXED ETHER COMPOSITIONS CONTAINING OLIGOMERS OF POLYFUNCTIONAL PHOSPHINE OXIDES: FLAME RETARDANTS FOR POLYMERS

The present invention relates to a mixture of polyether derivatives of polyfunctional hydroxyalkyl phosphine oxides, i.e., a mixture of oligomers derived from tris- and/or bis-3-hydroxyalkyl phosphine oxides and to a method for the manufacture of such ether derivatives. Such mixed polyethers may be used as fire retardant additives for thermoplastic and thermosetting resins such as the polyamide resins and polyphenylene oxide resins.

Simple, low molecular weight ethers of phosphine oxides have been described in the prior art. Monomeric ether derivatives of hydroxymethyl phosphine oxides have been derived from chloromethyl phosphines and chloromethyl phosphine oxides by reacting the same with sodium alkoxide or sodium phenoxide. This reaction is described in German Offenlegungsschrift No. 2,258,662. G. Borisov also describes a low molecular weight polyether made from methyl bischloromethyl phosphine oxide and the sodium salt of bisphenol A in Vysokonol Soedim, Sect. A. 15, 275 (1973). Other monomeric ethers are described in U.S. Pat. No. 3,883,474 made from dimethyl chloromethyl phosphine oxide and sodium phenoxide (derived from halogen containing phenols and bisphenols). These latter monomeric phosphine oxide ethers are said to be useful fire retardant additives in polyester resins.

Simple monomeric ether derivatives of chloroethyl phosphine oxides obtained by the reaction of such compounds with sodium alkoxide are described by L. Maier in Phosphorus 1, 245–249 (1972). The reaction of hydroxybutyl dialkyl phosphine oxide with alkylene oxides is referred to in U.S. Pat. No. 3,267,149. The phosphine oxide ethers of the present invention, however, contain repeating phosphine oxide groups in the polymer and may also be distinguished structurally over many of the ether derivatives of phosphine oxides known heretofore in that the ether groups (and the terminal hydroxyl groups) are either two or three carbon atoms removed from the phosphorus atom. Such phosphine oxides are superior fire retardants and may be characterized as more stable than other previously known phosphine oxides wherein residual hydroxyl groups are on the α-carbon atom.

In accordance with the present invention, mixed ether compositions containing oligomers of polyhydroxyalkyl phosphine oxide are manufactured by heating the phosphine oxide at a temperature of from about 139° C. to about 200° C. in the presence of an acid catalyst and separating the water formed during etherification from the reaction mixture. Aliphatic, cycloaliphatic and aromatic alcohols having one or more hydroxyl groups and halogenated derivatives of such alcohols can be added to the phosphine oxide to form an ether of the phosphine oxide with the added alcohol. Depending upon the reactants employed, the mixed ether compositions of the present invention may contain oligomers having the structure:

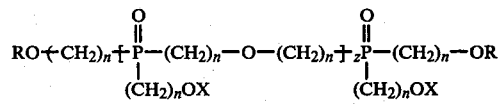

wherein R is a divalent radical derived from a polyfunctional alcohol, Z is 1, 2 or 3, n is 2 or 3, and X may be the same or a different radical selected from the group consisting of hydrogen and

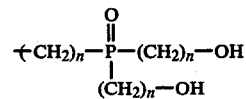

radicals.

Another novel mixed ether composition that is claimed in the present invention is derived from a hydroxyalkyl phosphine oxide and a monohydric aliphatic, cycloaliphatic, aromatic, halogenated aliphatic, halogenated cycloaliphatic or halogenated aromatic alcohol and contains oligomers having the structure:

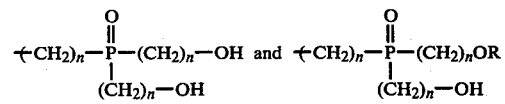

wherein Z is 1, 2 or 3, n is 2 or 3, R is the same or a different radical selected from the group consisting of hydrogen, aliphatic, cycloaliphatic, aromatic, halogenated aliphatic, halogenated cycloaliphatic and halogenated aromatic radicals and X may be the same or a different radical selected from the group consisting of hydrogen, R, $$+CH_2)_n-\overset{O}{\underset{(CH_2)_n-OH}{P}}-(CH_2)_n-OH \text{ and } +CH_2)_n-\overset{O}{\underset{(CH_2)_n-OH}{P}}-(CH_2)_nOR$$

radicals.

Yet another novel mixed ether composition that forms a part of the present invention is derived from a bis-hydroxyalkyl phosphine oxide and contains oligomers having the structure:

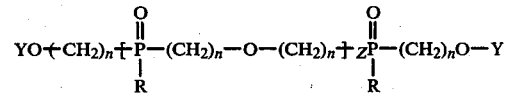

wherein R is a radical selected from the group consisting of aliphatic and cycloaliphatic radicals, Z is 1, 2 or 3, n is 2 or 3 and Y is a radical selected from the group consisting of hydrogen, aliphatic, cycloaliphatic, aromatic, halogenated aliphatic, halogenated cycloaliphatic and halogenated aromatic radicals.

Still another respect of the present invention are mixed ether compositions derived from a bis-hydroxyalkyl phosphine oxide and a polyfunctional alcohol which ether compositions contain oligomers having the structure:

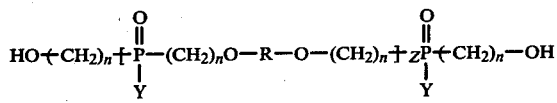

wherein R is a divalent radical derived from a polyfunctional alcohol, Z is 1, 2 or 3, n is 2 or 3, and Y is a radical selected from the group consisting of aliphatic and cycloaliphatic radicals.

The mixed ether compositions of the present invention are excellent fire retardant additives and increase the fire resistance of thermoplastic and thermosetting resins. These mixed ether compositions are particularly effective when added to the polyamide and polyphenylene oxide resins.

Preferred mixed ether compositions derived from bis-hydroxyalkyl phosphine oxide and a polyfunctional alcohol contain oligomers having the structure:

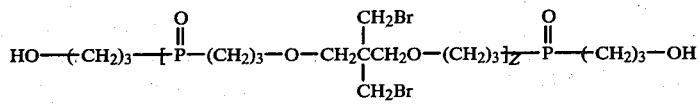

wherein Z is 1, 2 or 3, and Y is a radical selected from the group consisting of aliphatic and cycloaliphatic radicals.

The mixed ethers of the present invention may be made by condensing a bis-hydroxyalkyl phosphine oxide or a trishydroxyalkyl phosphine oxide or mixtures thereof by heating in the presence of an acid catalyst. The preferred hydroxyalkyl phosphine oxide is tris-(3-hydroxypropyl) phosphine oxide although the 2-hydroxyethyl phosphine oxides will also condense to form oligomeric ethers. Other monohydric and polyhydric aliphatic, aromatic and cycloaliphatic alcohols and halogenated derivatives of such alcohols may also be added to the hydroxyalkyl phosphine oxides to form an ether of the phosphine oxide with the added alcohol.

Inert liquids such as xylene may be added to the reaction mixture to control heating and remove water formed during the reaction by forming an azeotrope. If xylene is present, the etherification reaction will occur at refluxing temperatures, i.e., at about 139° C.-144° C. However, xylene is not a suitable additive for lower boiling alcohols and polyols appreciably soluble in xylene. Under these conditions, it is preferred that higher temperatures (170° C.-200° C.) may be used to remove the water formed by the etherification reaction. The progress of the reaction may be followed by thin layer chromatography and by the amount of water removed during the reaction. When tris-hydroxyalkyl phosphine oxides are heated together by themselves or with polyols having two or more hydroxyl groups, care must be taken to stop the reaction before gelation by crosslinking occurs. The mixed ethers range from low to high viscosity oils which may be soluble in water or in hydrocarbons depending upon the reactants used.

Sulfuric acid or some other sulfur acid such as methanesulfonic acid or p-toluenesulfonic acid are the catalysts of choice for this etherification procedure, although other acid catalysts may be used. Catalyst levels of 0.5%-10% (molar based on the phosphine oxide) can be used, however, 1%-2% levels are preferred. After the reaction, the catalyst may be left in the reaction mixture or neutralized with sodium hydroxide. If neutralization is done, the sodium sulfate may be precipitated using methanol, or may be left in the reaction mixture.

As indicated above, the acid catalyzed etherification may be run on hydroxyalkyl phosphine oxides with or without other added hydroxyl-containing materials. Other alcohols and polyols that may be added to prepare the mixed ether compositions include ethylene glycol, neopentyl glycol, pentaerythritol, glycerine, trimethylol propane, dibromoneopentylglycol, tribromoneopentyl alcohol, decanol, cyclohexyl alcohol, butyl cellosolve, butyl carbitol, straight chain 1-alcohols, 2,3-dibromopropanol, phenol, tribromophenol, bisphenol A, tetrabromobisphenol A, etc.

The ether/polyether-containing phosphine oxides described herein may be used as flame retardant additives for both thermoplastic and thermoset resin systems and foams. Such resins could include polyamides, polyphenylene oxide-polystyrene blends, polybutylene terephthalate, polyethylene terephthalate, styrenics, styrene containing resins, polyacrylates, unsaturated polyesters, polyurethanes, polyolefins, polysulfones, etc. They appear to be most effective in polyamide, polyethylene oxide and polyester systems. For example, Nylon-66 containing 21 parts of a tris-3-hydroxypropyl phosphine oxide/pentaerythritol polyether obtained a 94 V-O rating on the UL-94 vertical burn test. The UL-94 vertical burn test is described in Example VII below. Good compatability with the resins was found in all cases.

The following Examples will more fully illustrate the invention. In these Examples reacting quantities are expressed in parts by weight unless otherwise indicated.

EXAMPLE I

A mixture of 22.4 g (0.1 mole) of tris-3-hydroxypropyl phosphine oxide, 3.4 g (0.025 mole) of pentaerythritol and 0.2 g (0.002 mole) of sulfuric acid and 100 g of xylene (a mixture is isomers) is placed in a round bottom flask equipped with a magnetic stirrer, Dean Stark trap with a Friedrichs condenser and nitrogen inlet. This mixture is heated in an oil bath to reflux temperature for 16 hours. The mixture at that time has two liquid phases, the lower phase containing unreacted phosphine oxide, pentaerythritol, and a mixed ether composition containing oligomers. A total of 2.0 g of water is removed over the 16 hour period. Thin layer chromatography (silica gel in chloroform/methanol 4/1) showed a trace of the tris-(3-hydroxypropyl) phosphine oxide, a large spot at the bottom of the plate, and a few other spots with very low $R_f$. The xylene layer is decanted from the cooled reaction mixture and the residue dissolved in methanol/water (1/1) 200 ml, neutralized to pH 8.0 with 5% sodium hydroxide, filtered through a medium sintered glass frit, and the solvent stripped on a rotary evaporator. The remaining viscous oil is dried in a vacuum oven at 60° C. for 16 hours. The resulting slightly yellow viscous oil weighs 23.0 g (96% yield) and has a 30% aqueous solution viscosity at 20° C. of 34.5 centistokes. The proton nuclear magnetic resonance spectrum of the product showed two broad multiplets at $\delta 1.9$ and $\delta 3.6$ with relative areas of 12/8 which is what is expected for a product from a 4/1 mixture of tris-(3- hydroxypropyl) phosphine oxide and pentaerythritol. The number average molecular weight, determined by vapor phase osmometry, was 865. Elemental analysis of the product is: C, 50.21; H, 9.31; P, 12.30.

In a similar manner, mixed ether compositions containing oligomers having the structure:

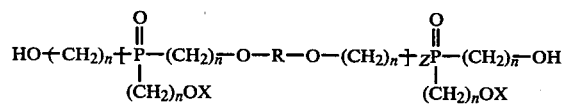

wherein R is a divalent radical derived from a polyfunctional alcohol, Z is an integer greater than 0 and smaller than 4, n is 2 or 3, and X may be the same or a different radical selected from the group consisting of hydrogen and

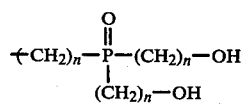

may be prepared.

In the phosphine oxide ethers of the present example, the divalent radical —R— may be derived from a diol such as ethylene glycol, dibromoneopentyl glycol, neopentyl glycol, bisphenol A, tetrabromobisphenol A, or a polyol such as pentaerythritol, glycerine, trimethylolpropane. Such mixed ether compositions may be provided by reacting a dihydric or polyhydric alcohol with a tris-(2-ethyl) or a tris-(3-propyl) phosphine oxide.

EXAMPLE II

A mixture of 50.1 parts of tris-(3-hydroxypropyl) phosphine oxide, 0.2 parts of sulfuric acid and 100 parts of 0-xylene are heated to reflux temperature in a vessel that is equipped with a Dean Start trap for water removal, a stirrer for agitation and a nitrogen inlet. After 6 hours, 2.0 parts of water have been removed. Thin layer chromatography shows a small amount of tris-hydroxypropyl phosphine oxide remaining and 2 large spots at the bottom of the plate. Forty-seven parts by weight of a clear viscous oil are separated from this reaction mixture by the method described in Example I above. This material is clearly less viscous than the product of Example I and is characterized by a solution viscosity (30% solids in water) at 20° C. of 6.0 cs. The proton nuclear magnetic resonance spectrum of this material is identical to that of the tris-(3-hydroxypropyl) phosphine oxide.

EXAMPLE III

A mixture of 134.4 parts (0.6 mole) of tris-(3-hydroxypropyl) phosphine oxide, 249 parts (0.95 mole) of dibromoneopentyl glycol, 0.5 parts of sulfuric acid and 400 parts of mixed isomers of xylene are heated to reflux temperature under nitrogen with water removal as described in Example I. Heating is continued for 7 hours in which time 13 parts of water have been removed by azeotropic distillation.

The xylene layer is decanted and stripped to give 20 parts of unreacted dibromoneopentyl glycol. The rest of the reaction mixture is worked up as described above in Example I to give 335.9 parts (96% yield) of a slightly turbid viscous yellow oil. Thin layer chromatography shows essentially no tris-(3-hydroxypropyl) phosphine oxide remaining and most of the product mixture had very low $R_f$. Elemental analysis of the product is: C, 32.91; H, 5.40; P, 5.15; Br, 38.32.

EXAMPLE IV

A mixture of 22.4 parts (0.1 mole) of tris-(3-hydroxypropyl) phosphine oxide, 49.0 parts (0.3 mole) of n-decanol, and 0.2 parts of sulfuric acid are heated under nitrogen in a vessel similar to that described in Example II at 150° C. for 16 hours. The reaction mixture becomes homogeneous and thin layer chromatography shows no residual tris-(3-hydroxypropyl) phosphine oxide left but does indicate the presence of 5 new compounds. The temperature of the reaction mixture is raised to 200° C. for 2 hours with no change in either appearance or the thin layer chromatography of the reaction mixture. The unreacted decanol (26.3 parts) is removed by vacuum distillation. The residue is soluble in toluene and insoluble, or only slightly soluble in water. The residue is dissolved in 800 parts of toluene, washed with 5% sodium carbonate, dried over magnesium sulfate, filtered and the solvent stripped under vacuum to give 38.6 parts of a cloudy yellow viscous oil. The proton nuclear magnetic resonance spectrum of this composition shows the presence of the decyl group and indicates that 1.25 decyl groups are added per phosphine oxide molecule. Elemental analysis calculated for $C_{21.5}H_{46}O_4P$ (1.25 decyl group) per phosphorous atom: C, 64.66; H, 11.53; P, 7.77. Found: C, 64.49; H. 10.89; P, 7.00.

EXAMPLE V

A mixture of 24.8 parts (0.1 mole) of cyclohexyl bis-3-hydroxypropyl phosphine oxide, 10.4 parts (0.1 mole) of neopentyl glycol, 0.2 parts of sulfuric acid and 100 parts of xylene are heated to reflux under nitrogen with water being removed as described above. After heating for 30 hours, 3.1 parts of water had been removed. The mixture is a single phase mixture while hot, but on cooling becames translucent reflecting yellow and blue colors. Xylene is stripped from the mixture, and the residue is dissolved in methanol/water, neutralized, filtered, stripped and dried in a vacuum oven at 60° C. overnight. The product, 30.1 parts (95% yield) is a yellow viscous oil. Thin layer chromatography shows 2 main spots with $R_f$ near that of the starting material. The proton nuclear magnetic resonance spectrum shows four signals at $\alpha 1.1$–2.2 (broad multiplet), $\alpha 0.9$ (singlet), $\alpha 3.35$ (singlet), $\alpha 3.4$–3.7 (broad multiplet) with relative areas of 5.5, 1.5, 1, 1 (theoretical ratio is 4.8, 1.5, 1, 1). Elemental analysis of the product is: C, 58.36; H, 10.00; P, 9.75.

EXAMPLE VI

A mixture of 22.4 parts (0.1 mole) of tris-(3-hydroxypropyl) phosphine oxide, 40.8 parts (0.075 mole) of tetrabromobisphenol A and 0.5 parts of sulfuric acid is heated to 170° C. in a container. A stream of nitrogen is bubbled through the reaction mixture over a period of 2 hours to remove the water formed by etherification. The reaction product, upon cooling is a friable glass which, by thin layer chromatography, showed no remaining phosphine oxide starting material. This glass is ground, dissolved in aqueous methanol, neutralized, filtered and stripped to dryness to give an amber solid weighing 60.8 parts. Unreacted tetrabromobisphenol A is removed by extraction with refluxing chloroform. The amount of residue which remains after chloroform extraction (37.7 parts) corresponds to a ratio of hydroxypropyl phosphine oxide to bisphenol reacted of about 3:1. Differential scanning calorimetry for this product indicates that the composition is stable up to a temperature of about 310° C. at which temperature a sharp exotherm occurs. By contrast, the starting materials have broad endotherms starting at about 250° C.

EXAMPLE VII

Hydroxypropyl phosphine oxide ether derivatives are used as flame retardants for thermoplastic resins. Phosphine oxide derivatives are added to the indicated thermoplastics (see Tables I and II) in amounts indicated as amounts per hundred parts of resin (PHR) and dispersed throughout the resin. Mixing of the additive and resin was accomplished in a Brabender type mixer (Haake Rheomix Model 600 with Reocord EU 10 attachment, manufactured by Haake, Inc., 244 Saddle River Rd, Saddle Brook, N.J. 07662). Mixing takes place at the indicated temperatures. Polymer samples were tested for flammability according to procedures established by the Underwriter Laboratories Bulletin No. 94, Standard for Tests for Flammability of Plastic Materials for Parts in Devices and Appliances, Second Edition, Second Impression (as revised to February, 1974) dated July 30, 1976. The Vertical Burning Test for classifying materials 94 V-O, 94 V-1, or 94 V-2 and described in Section 3 of this publication were used. In this test, the V-O rating indicates the best flame resistance and V-2 rating the poorest flame resistance. Oxygen index tests are run according to ASTM D2683. The flame retardant effect is summarized in Tables I and II.

TABLE I
TEST RESULTS FOR TRIS-(3-HYDROXYPROPYL) PHOSPHINE OXIDE ETHER DERIVATIVE OF EXAMPLE I IN THERMOPLASTICS

| Resin | Parts Per Hundred Additive | UL-94[1] Rating | Average Burn Time, Secs. |
|---|---|---|---|
| Nylon 66[2] | — | Complete Burn | |
| Nylon 66[2] | 21 | V-0 | 4.1 |
| Modified PPO/PS[3,5] | 5 | V-1 | 10.2 |
| PBT[4,6] | 10.3* | V-1 | 10.3 |

[1] ⅛" thick samples
[2] Mixing temperature 260° C.–250° C.
[3] Mixing temperature 225° C.
[4] Mixing temperature 235° C.–255° C.
[5] Noryl (35% polyphenylene oxide, 65% polystyrene)
[6] Polybutylene terephthalate
*10.3 parts per hundred tris-(3-hydroxypropyl) phosphine oxide ether derivative of Example I + 10.7 parts per hundred of decabromodiphenylene oxide

TABLE II
TEST RESULTS OF POLY-TRIS-(3-HYDROXYPROPYL) PHOSPHINE OXIDE OF EXAMPLE II IN THERMOPLASTICS

| Sample | Resin | Parts Per hundred of Poly-Tris-(3-Hydroxypropyl) Phosphine Oxide | Oxygen Index |
|---|---|---|---|
| 1 | Nylon 66[2] | — | 22.9 |
| 2 | Nylon 66[2] | 17 | 27.1 |
| 3 | Nylon 66[2] | 21 | 26.0 |
| 4 | Nylon 66[2] | 25 | 26.8 |
| 5 | Modified PPO/PS[3,5] | — | 24.9 |
| 6 | Modified PPO/PS[3,5] | 4 | 30.4 |
| 7 | Modified PPO/PS[3,5] | 6 | 29.3 |
| 8 | PBT[4,6] | 9* | — |

| Sample | UL-94[1] Rating | Burn Time Secs. | Vicat Softening |
|---|---|---|---|
| 1 | Complete Burn | | 249° C. |
| 2 | V-1 | 8.8 | 238° C. |
| 3 | V-0 | 3.4 | 240° C. |
| 4 | V-0 | 2.5 | 237° C. |
| 5 | Complete Burn | | |
| 6 | V-1 | 11.8 | — |
| 7 | V-1 | 7.4 | — |
| 8 | V-1 | 11 | — |

[1] 1/18" thick samples
[2] Mixing temperature 260° C.–250° C.
[3] Mixing temperature 225° C.
[4] Mixing temperature 235° C.–250° C.
[5] Noryl 731 (35% polyphenylene oxide, 65% polystyrene)
[6] Polybutylene terephthalate
*9 parts per hundred poly-tris-(3-hydroxypropyl) phosphine oxide of Example II + 12 parts per hundred decabromodiphenylene oxide

TABLE III
VOLATILITY DATA FOR HYDROXYPROPYL PHOSPHINE OXIDES AND POLYETHER DERIVATIVES

| Sample | Temp. Start Major Wt. Loss | Temp. 50% Wt. Loss | Remarks |
|---|---|---|---|
| THPPO[2] | 235° C. | 330° C. | No char |
| poly-THPPO[2] | 300° C. | 395° C. | Foam and char forms |
| BHPPO[1] | 150° C. | 300° C. | No char |
| poly-BHPPO[1] | 225° C. | 360° C. | Foam and char forms |

[1] sec-butyl bis-(3-hydroxypropyl) phosphine oxide
[2] tris-(3-hydroxypropyl) phosphine oxide

I claim:
1. Mixed ether compositions containing oligomers having the structure:

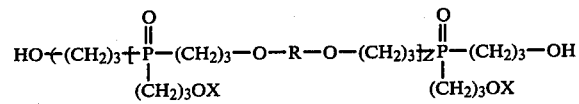

wherein R is an organic residue derived from a polyhydric alcohol, said R being a divalent radical selected from the class consisting of a hydrocarbon radical, a halogenated hydrocarbon radical and

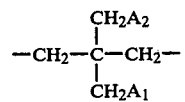

wherein $A_1$ and $A_2$ are radicals selected from the group consisting of hydroxyl, hydrogen, bromine and

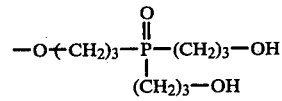

radicals provided that when $A_1$ is

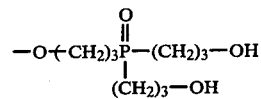

$A_2$ is hydroxyl; when $A_1$ is hydroxyl $A_2$ is hydroxyl; when $A_1$ is hydrogen $A_2$ is hydrogen; and when $A_1$ is bromine $A_2$ is bromine, Z is 1, 2 or 3, and X may be the same or a different radical selected from the group consisting of hydrogen and

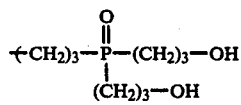

radicals.

2. The mixed ether compositions of claim 1 containing oligomers having the structure:

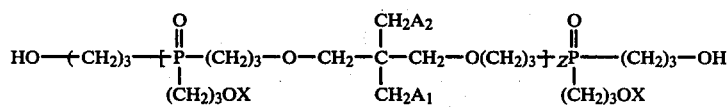

wherein Z is an integer greater than 0 and smaller than 4, X may be the same or a different radical selected from the group consisting of hydrogen and

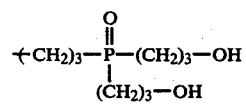

and $A_1$ and $A_2$ are radicals selected from the group consisting of hydroxyl, hydrogen, bromine and

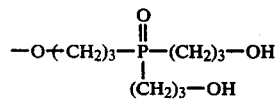

radicals provided that when $A_1$ is

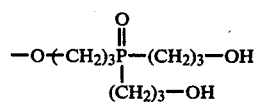

$A_2$ is hydroxyl; when $A_1$ is hydroxyl $A_2$ is hydroxyl; when $A_1$ is hydrogen $A_2$ is hydrogen; and when $A_1$ is bromine $A_2$ is bromine.

3. The mixed ether compositions of claim 2 wherein $A_1$ and $A_2$ are bromine radicals.

4. The mixed ether compositions of claim 2 wherein $A_1$ and $A_2$ are hydrogen radicals.

5. The mixed ether compositions of claim 2 wherein $A_2$ is a hydroxyl radical and $A_1$ is a

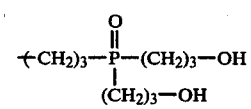

radical.

6. The mixed ether compositions of claim 2 wherein $A_1$ and $A_2$ are hydroxyl radicals.

7. The mixed ether compositions of claim 1 wherein the divalent radical R is a

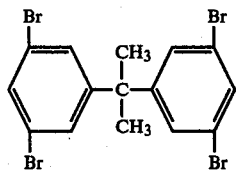

radical.

8. A flame retardant resin composition comprising a resin containing from about 5 to about 25 parts per hundred of the mixed ether compositions defined by claim 1.

9. A flame retardant resin composition comprising a resin containing from about 5 to about 25 parts per hundred of the mixed ether compositions defined by claim 2.

10. A flame retardant resin composition comprising a resin containing from about 5 to about 25 parts per hundred of the mixed ether compositions defined by claim 3.

11. A flame retardant resin composition comprising a resin containing from about 5 to about 25 parts per hundred of the mixed ether compositions defined by claim 4.

12. A flame retardant resin composition comprising a resin containing from about 5 to about 25 parts per hundred of the mixed ether compositions defined by claim 5.

13. A flame retardant resin composition comprising a resin containing from about 5 to about 25 parts per hundred of the mixed ether compositions defined by claim 6.

14. A flame retardant resin composition comprising a resin containing from about 5 to about 25 parts per hundred of the mixed ether compositions defined by claim 7.

15. A flame retardant resin composition comprising a nylon resin containing from about 5 to about 25 parts per hundred of the mixed ether compositions defined by claim 1.

16. A flame retardant resin composition comprising a polyphenylene oxide-polystyrene resin containing from about 10 parts to about 25 parts per hundred of the mixed ether compositions defined by claim 1.

17. A flame retardant resin composition comprising a polyethylene terephthalate resin containing from about 10 to about 25 parts per hundred of the mixed ether compositions defined by claim 1.

18. A flame retardant resin composition comprising a polybutylene terephthalate resin containing from about 10 to about 25 parts per hundred of the mixed ether compositions defined by claim 1.

19. Mixed ether compositions containing oligomers having the structure:

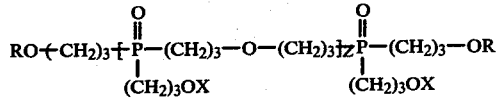

wherein Z is 1, 2 or 3, R is the same or a different radical selected from the group consisting of hydrogen, aliphatic alkoxyaliphatic, cycloaliphatic, aromatic, halogenated aliphatic, halogenated cycloaliphatic and halogenated aromatic radicals and X may be the same or a different radical selected from the group consisting of hydrogen, R,

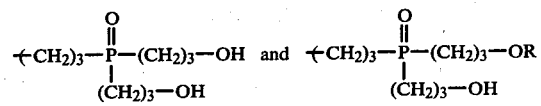

radicals.

20. The mixed ether compositions of claim 19 wherein R is a radical selected from the group consisting of hydrogen and

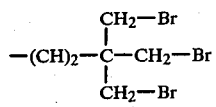

radicals.

21. The mixed ether compositions of claim 19 wherein R is a radical selected from the group consisting of hydrogen and decyl radicals.

22. The mixed ether compositions of claim 19 wherein R is a radical selected from the group consisting of hydrogen and 2,3-dibromopropyl radicals.

23. The mixed ether compositions of claim 19 wherein R is a radical selected form the group consisting of hydrogen and butoxyethyl radicals.

24. The mixed ether compositions of claim 19 wherein R is a radical selected from the group consisting of hydrogen and

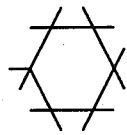

radicals.

25. The mixed ether compositions of claim 19 wherein R is a radical selected from the group consisting of hydrogen and

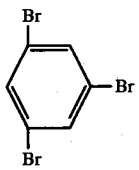

radicals.

26. The mixed ether compositions of claim 19 wherein R is a radical selected from the group consisting of hydrogen and butoxyethoxyethyl radicals.

27. A flame retardant resin composition comprising a resin containing from about 5 to about 25 parts per hundred of the mixed ether compositions defined by claim 19.

28. A flame retardant resin composition comprising a resin containing from about 5 to about 25 parts per hundred of the mixed ether compositions defined by claim 20.

29. A flame retardant resin composition comprising a resin containing from about 5 to about 25 parts per hundred of the mixed ether compositions defined by claim 22.

30. A flame retardant resin composition comprising a resin containing from about 5 to about 25 parts per hundred of the mixed ether compositions defined by claim 23.

31. A flame retardant resin composition comprising a resin containing from about 5 to about 25 parts per hundred of the mixed ether compositions defined by claim 24.

32. A flame retardant resin composition comprising a resin containing from about 5 to about 25 parts per hundred of the mixed ether compositions defined by claim 25.

33. A flame retardant resin composition comprising a resin containing from about 5 to about 25 parts per hundred of the mixed ether compositions defined by claim 26.

34. A flame retardant resin composition comprising a nylon resin containing from about 5 to about 25 parts per hundred of the mixed ether compositions defined by claim 107.

35. A flame retardant resin composition comprising a polyphenylene oxide-polystyrene resin containing from about 10 parts to about 25 parts per hundred of the mixed ether compositions defined by claim 19.

36. A flame retardant resin composition containing a polyethylene terephthalate resin containing from about 10 to about 25 parts per hundred of the mixed ether compositions defined by claim 19.

37. A flame resistant resin composition comprising a polybutylene terephthalate resin containing from about 10 to about 25 parts per hundred of the mixed ether compositions defined by claim 19.

38. Mixed ether compositions containing oligomers having the structure:

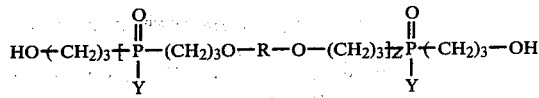

wherein R is an organic residue derived from a polyhydric alcohol, said R being a divalent radical selected from the class consisting of a hydrocarbon radical, a halogenated hydrocarbon radical and

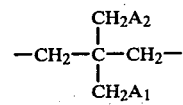

wherein $A_1$ and $A_2$ are radicals selected from the group consisting of hydroxyl, hydrogen, bromine and

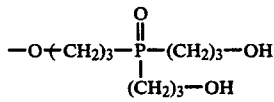

radicals provided that when $A_1$ is

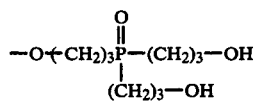

$A_2$ is hydroxyl; when $A_1$ is hydroxyl $A_2$ is hydroxyl; when $A_1$ is hydrogen $A_2$ is hydrogen; and when $A_1$ is bromine $A_2$ is bromine, Z is 1, 2 or 3, and Y is a radical selected from the group consisting of aliphatic and cycloaliphatic radicals.

39. The mixed ether compositions of claim 38 containing oligomers having the structure:

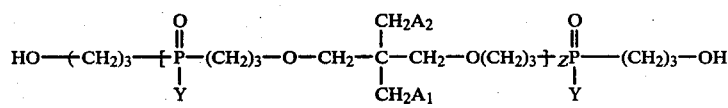

wherein Y is a radical selected from the group consisting of aliphatic and cycloaliphatic radicals, Z is 1, 2 or 3, and $A_1$ and $A_2$ are radicals selected from the group consisting of hydroxyl, hydrogen, bromine and

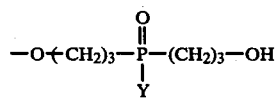

radicals, provided that when $A_1$ is

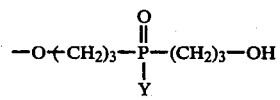

$A_2$ is hydroxyl; when $A_1$ is hydroxyl $A_2$ is hydroxyl; when $A_1$ is hydrogen $A_2$ is hydrogen; and when $A_1$ is bromine $A_2$ is bromine.

40. The mixed ether compositions of claim 39 wherein $A_1$ and $A_2$ are bromine radicals.

41. The mixed ether compositions of claim 39 wherein $A_1$ and $A_2$ are hydrogen radicals.

42. The mixed ether compositions of claim 39 wherein $A_2$ is a hydroxyl radical and $A_1$ is a

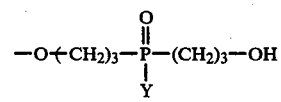

radical.

43. The mixed ether compositions of claim 39 wherein $A_1$ and $A_2$ are hydrogen radicals.

44. The mixed ether compositions of claim 39 wherein R is the divalent radical

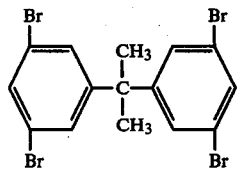

45. The mixed ether compositions of claim 39 wherein Y is a butyl radical.

46. The mixed ether compositions of claim 39 wherein Y is a cyclohexyl radical.

47. A flame retardant resin composition comprising a resin containing from about 5 to about 25 parts per hundred of the mixed ether compositions defined by claim 38.

48. A flame retardant resin composition containing a resin containing from about 5 to about 25 parts per hundred of the mixed ether compositions defined by claim 39.

49. A flame retardant resin composition containing a resin containing from about 5 to about 25 parts per hundred of the mixed ether compositions defined by claim 40.

50. A flame retardant resin composition containing a resin containing from about 5 to about 25 parts per hundred of the mixed ether compositions defined by claim 41.

51. A flame retardant resin composition containing a resin containing from about 5 to about 25 parts per hundred of the mixed ether compositions defined by claim 42.

52. A flame retardant resin composition containing a resin containing from about 5 to about 25 parts per hundred of the mixed ether compositions defined by claim 43.

53. A flame retardant resin composition containing a resin containing from about 5 to about 25 parts per hundred of the mixed ether compositions defined by claim 44.

54. A flame retardant resin composition containing a resin containing from about 5 to about 25 parts per hundred of the mixed ether compositions defined by claim 45.

55. A flame retardant resin composition containing a resin containing from about 5 to about 25 parts per hundred of the mixed ether compositions defined by claim 46.

56. A flame retardant resin composition comprising a polyamide resin containing from about 10 to about 25 parts per hundred of the mixed ether compositions defined by claim 38.

57. A flame retardant resin composition comprising a propylene oxide-polystyrene resin containing from about 10 to about 25 parts per hundred of the mixed ether compositions defined by claim 38.

58. A flame resistant resin composition comprising a polyethylene terephthalate resin containing from about 10 to about 25 parts per hundred of the mixed ether compositions defined by claim 38.

59. A flame resistant resin composition comprising a polybutylene terephthalate resin containing from about 10 to about 25 parts per hundred of the mixed ether compositions defined by claim 38.

60. Mixed ether compositions containing oligomers having the structure:

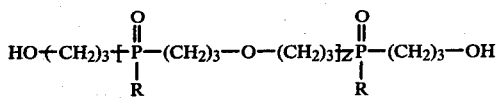

wherein R is a radical selected from the group consisting of aliphatic and cycloaliphatic radicals and Z is 1, 2 or 3.

61. The mixed ether composition of claim 60 wherein R is a butyl radical.

62. The mixed ether composition of claim 60 wherein R is a cyclohexyl radical.

63. A flame retardant resin composition comprising a resin containing from about 5 to about 25 parts per hundred of the mixed ether compositions defined by claim 60.

64. A flame retardant resin composition comprising a resin containing from about 5 to about 25 parts per hundred of the mixed ether compositions defined by claim 61.

65. A flame retardant resin composition comprising a resin containing from about 5 to about 25 parts per hundred of the mixed ether compositions defined by claim 62.

66. A flame retardant resin composition comprising a nylon resin containing from about 5 to about 25 parts per hundred of the mixed ether compositions defined by claim 61.

67. A flame retardant resin composition comprising a polyphenylene oxide-polystyrene resin containing from about 5 to about 25 parts per hundred of the mixed ether compositions defined by claim 61.

68. A flame retardant resin composition comprising a polyethylene terephthalate resin containing from about 5 to about 25 parts per hundred of the mixed ether compositions defined by claim 61.

69. A flame retardant resin composition comprising a polybutylene terephthalate resin containing from about 5 to about 25 parts per hundred of the mixed ether compositions defined by claim 61.

70. A flame retardant resin composition comprising a nylon resin containing from about 5 to about 25 parts per hundred of the mixed ether compositions defined by claim 62.

71. A flame retardant resin composition comprising a polyphenylene oxide-polystyrene resin containing from about 10 parts to about 25 parts per hundred of the mixed ether compositions defined by claim 62.

72. A flame retardant resin composition comprising a polyethylene terephthalate resin containing from about 10 to about 25 parts per hundred of the mixed ether compositions defined by claim 62.

73. A flame retardant resin composition comprising a polybutylene terephthalate resin containing from about 10 to about 25 parts per hundred of the mixed ether compositions defined by claim 62.

* * * * *

UNITED STATES PATENT AND TRADEMARK OFFICE
CERTIFICATE OF CORRECTION

PATENT NO. : 4,377,653
DATED : March 22, 1983
INVENTOR(S) : Edward R. Fretz, Jr.

It is certified that error appears in the above-identified patent and that said Letters Patent are hereby corrected as shown below:

Column 4, line 44, "(a mixture is isomers)" should read --(a mixture of isomers)--.

Column 7, line 30, "D2683" should read --D2863--.
Column 12, line 34, "107" should read --19--.

Signed and Sealed this

Fourth Day of September 1984

[SEAL]

Attest:

Attesting Officer

GERALD J. MOSSINGHOFF

Commissioner of Patents and Trademarks